United States Patent [19]

Hall et al.

[11] 4,113,880

[45] Sep. 12, 1978

[54] 2'-HYDROXY-3'-CARBOXY-5'-NITROOX-ANILATE COMPOUNDS, COMPOSITIONS, AND METHODS OF USE

[75] Inventors: Charles M. Hall; John B. Wright, both of Kalamazoo, Mich.

[73] Assignee: The Upjohn Company, Kalamazoo, Mich.

[21] Appl. No.: 742,438

[22] Filed: Nov. 17, 1976

[51] Int. Cl.² .............................................. A61K 31/24
[52] U.S. Cl. .................................. 424/309; 560/22; 562/437; 424/317
[58] Field of Search .................... 260/471 A, 519; 424/309

[56] References Cited

U.S. PATENT DOCUMENTS 3,511,804  5/1970  Duennenberger .............. 260/45.85
3,966,965  6/1976  Sellstedt et al. ................. 424/309

FOREIGN PATENT DOCUMENTS 2,525,226  1975  Fed. Rep. of Germany.
994,714  6/1965  United Kingdom.

OTHER PUBLICATIONS

Tiere, G.; "Rec. Trav. Chim.", vol. 52, pp. 420–424, (1933).

Primary Examiner—Donald G. Daus
Assistant Examiner—Lisa Jones
Attorney, Agent, or Firm—Martin B. Barancik

[57] ABSTRACT

Novel compounds of the formula

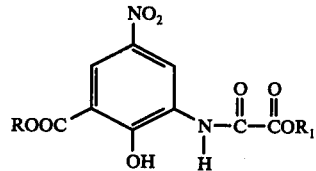

where R is hydrogen, a physiologically acceptable metal or amine cation, or alkyl of one to eight carbon atoms, inclusive, $R_1$ is hydrogen, a physiologically acceptable metal or amine cation, or alkyl of one to eight carbon atoms, inclusive, are formulated into pharmaceutical compositions useful for preventing allergic manifestations in sensitized mammals.

41 Claims, No Drawings

2'-HYDROXY-3'-CARBOXY-5'-NITROOXANILATE COMPOUNDS, COMPOSITIONS, AND METHODS OF USE

BRIEF SUMMARY OF THE INVENTION

It has now been discovered that novel compounds of Formula 1 are useful in the prophylatic treatment of sensitized mammals for allergy and anaphylactic reactions of a reagin or non-reagin mediated nature. The compounds are formulated with pharmaceutical carriers for oral, parenteral or inhalation means of administration.

DETAILED DESCRIPTION OF THE INVENTION

In accordance with this invention, there are provided compounds represented by Formula 1 and hereafter referred to as Group A

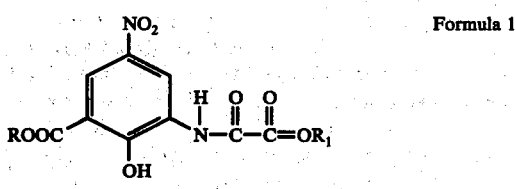

Formula 1 wherein R is hydrogen, a phsiologically acceptable metal or amine cation, or alkyl of one to eight carbon atoms, inclusive. $R_1$ is hydrogen, a physiologically acceptable metal or amine cation, or alkyl of one to eight carbon atoms, inclusive.

A further group of compounds, hereafter referred to as Group B, are the compounds of Group A wherein $R_1$ is alkyl of one to eight carbon atoms, inclusive.

Another group of compounds, hereafter referred to as Group C, are the compounds of Group B wherein R is the same as $R_1$.

A further group of compounds, hereafter referred to as Group D are the compounds of Group B wherein R is hydrogen.

Another group of compounds, hereafter referred to as Group E are the compounds of Group D wherein $R_1$ is from two to four carbon atoms, inclusive.

With respect to pharmaceutical compositions and a method of using those compositions, it is to be understood that the compounds of Group A, B, C, D, and E are a part of that aspect of the invention as well. Additionally, with respect to the composition and use aspects of the invention, the pharmaceutical composition and use of the compounds as suitable for oral means of administration is a further aspect of the invention. The pharmaceutical compositions and their use when employing a solid pharmaceutical carrier is a further aspect of the invention. Still further a liquid pharmaceutical carrier is another aspect, a still further aspect of the invention being a non-aqueous liquid carrier.

The preferred compound is where R is hydrogen and $R_1$ is ethyl.

As employed in the above disclosure and throughout the specification and claims, the phrase "alkyl of one to eight carbon atoms, inclusive" means methyl, ethyl, propyl, butyl, pentyl, hexyl, heptyl, octyl, and isomers thereof. Illustrative examples of isomers are isopropyl, tert-butyl, neopentyl, 2,2-dimethylbutyl, 2-methylhexyl, and 2,2,4-trimethylpentyl.

The phrase "physiologically acceptable amine salt" refers to amines which are accepted by mammals in an essentially non-toxic manner when administered to mammals in conjunction with the acid moiety of the invention. Illustrative of the amines are those derived from primary, secondary or tertiary amines. Examples of suitable amines are methylamine, dimethylamine, triethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, adamantylamines, and like aliphatic, cycloaliphatic, and araliphatic amines containing up to and including about eighteen carbon atoms as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-1-ethyl-1,3-propanediol, 2-amino-2-methyl-1-propanol, tris (hydroxymethyl)aminoethane, N-phenyslethanolamine, N-(p-tert-amylphenyl)diethanolamine, galactamine, N-methylglucamine, N-methylglucosamine, ephedrine, phenylephrine, epinephrine, procaine, and the like.

The term "physiologically acceptable metal" includes alkali metals such as sodium and potassium, alkaline earth metals such as calcium and magnesium, and other acceptable metals such as aluminum.

The compounds of the invention are prepared by standard means. When R is alkyl, the group may be placed on the carboxy substituent prior to the reaction of the aniline compound with the alkyl oxalyl chloride, alkyl being from one to eight carbon atoms, inclusive.

The following are examples of the invention. The examples are intended to illustrate and not to limit the invention.

EXAMPLE 1

Ethyl 2'-hydroxy-3'-carboxy-5'-nitrooxanilate hemihydrate

To 21.62 g. (0.1 mole) of 3-amino-5-nitrosalicylic acid monohydrate is added 250 ml. of benzene. The benzene is removed to azeotrope the water present. To the residue is added 100 ml. of dry dimethylformamide and 100 ml. of dry ethyl acetate. The solution is cooled in an ice-bath to 0°–5° C. and there is added 12.14 g (0.12 moles) of triethylamine followed by 16.38 g, (0.12 moles) of ethyl oxalyl chloride. The mixture is allowed to stand overnight at room temperature, the precipitate removed by filtration and the ethyl acetate removed from the filtrate by distillation in vacuo. The residue is poured into water (one liter) and the precipitate removed by filtration. There is obtained 26.9 g. of solid melting at 174° C. (dec.). Recrystallization from ethanol-water gives material melting at 176° C. (dec.).

Analysis Calcd. for: $C_{11}H_{10}N_2O_8 \cdot 1/2 \, H_2O$: C, 43.00; H, 3.61; N, 9.13% Found: C, 42.74; H, 3.54; N, 9.19%

EXAMPLE 2

In a manner similar to Example 1 compounds wherein R is hydrogen and $R_1$ is methyl, propyl, butyl, pentyl, hexyl, heptyl, octyl, isopropyl, tert-butyl, neopentyl, 2,2-dimethylbutyl, 2-methylhexyl, and 2,2,4- trimethylpentyl are prepared by reaction of 3-amino-5-nitrosalicyclic acid with, respectively, methyloxalyl chloride, propyl oxalyl chloride, butyl oxalyl chloride, pentyl oxalylchloride, hexyl oxalyl chloride, heptyl oxalyl chloride, octyl oxalyl chloride, isopropyl oxalyl chloride, tert-butyl oxalyl chloride, neopentyl oxalyl chloride, 2,2-dimethylbutyl oxalyl chloride, isoheptyl oxalyl chloride, and 2,2,4-trimethylpentyl oxalyl chloride.

EXAMPLE 3

Ethyl 2'-hydroxy-3'-carboxy-5'-nitrooxanilate.

The monooxamate prepared in Example 1 is heated to reflux with benzene. The azeotrope of benzene-water is removed, leaving ethyl-2'-hydroxy-3'-carboxy-5'-nitro oxanilate.

EXAMPLE 4

2'-hydroxy-3'-carboxy-5'-nitro oxanilic acid

Ethyl 2'-hydroxy-3'-carboxy-5'-nitro oxanilate or its monohydrate is stirred with an excess of 2N sodium hydroxide solution for 30 minutes. The solution is then acidified by the addition of 1N hydrochloric acid. The precipitate is removed by filtration and recrystallized from a suitable solvent.

EXAMPLE 5

Tris (hydroxymethyl)methylammonium 2'-hydroxy-3'-carboxy-5'-nitro oxanilate

2'-Hydroxy-3'-carboxy-5'-nitro oxanilic acid is dissolved in a solution containing one equivalent of tris(hydroxymethyl)amino methane (THAM) in water. The solution is evaporated to dryness and the residue is purified by recrystallization from a suitable solvent or trituration with ethanol.

EXAMPLE 6

Prior to the reaction of the nitrosalicylic acid of Example 1 with ethyl oxalyl chloride, the 3'-carboxy group is esterified with in-propanol and several drops of concentrated sulfuric acid under reflux conditions. The compound wherein R is propyl and $R_1$ is ethyl is recovered after the subsequent reaction steps.

EXAMPLE 7

Following the reaction sequence of Example 6, esters wherein R and $R_1$ are not the same are prepared. Illustrative of these compounds are:

| R | $R_1$ |
|---|---|
| $CH_3$ | $i-C_3H_7$ |
| $n-C_8H_{17}$ | $C_2H_5$ |
| $neo-C_5H_{11}$ | $t-C_4H_9$ |
| $n-C_6H_{13}$ | $n-C_7H_{15}$ |

EXAMPLE 8

The compounds of Example 7 are hydrolyzed in a manner similar to Example 4 and the di-acid recovered.

EXAMPLE 9

The diacid of Example 8 is converted to its physiologically acceptable metal or amine cation by the methods of Example 5. Compounds where R or $R_1$ is hydrogen or a physiologically acceptable metal or amine cation and the other variable is an alkyl group are also readily prepared.

The compositions of the present invention are presented for administration to humans and animals in unit dosage forms, such as tablets, capsules, pills, powders, granules, sterile parenteral solutions or suspensions, eye drops, oral solutions or suspensions, and oil-in-water and water-in-oil emulsions containing suitable quantities of the compound of Formula 1. The preferred method of administration is orally utilizing a compound of the formula wherein $R_1$ is ethyl. Compounds wherein $R_1$ is hydrogen are also quite effective.

For oral administration, either solid or fluid unit dosage forms can be prepared. For preparing solid compositions such as tablets, the compound of Formula 1 is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum, or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydroalcoholic (ethanol) vehicle with suitable sweeteners such as sugar and saccharin, together with an aromatic flavoring agent.

Suspensions can be prepared with an aqueous vehicle with the acid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions can be prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

For treatment of allergic conditions of the nose, such as rhinitis, compositions inhaled and adapted for contact with nasal linings are preferred.

Compositions for inhalation are of three basic types: (1) a powder mixture preferably micropulverized with particle size, preferably from about 1 to about 5 microns; (2) an aqueous solution or suspension to be sprayed with a nebulizer; and (3) an aerosol with volatile propellant in a pressurized container.

The powders are quite simply prepared by mixing a compound of the formula with a solid base which is compatible with lung tissue, preferably lactose. The powders are packaged in a device adapted to emit a measured amount of powder when inhaled through the mouth.

Aqueous solutions are prepared by dissolving the compound of the Formula 1 in water and adding salt to provide an isotonic solution and buffering to a pH compatible with inhalation. The solutions are dispersed in a spray device or nebulizer and sprayed into the mount while inhaling.

Aerosols are prepared by dispersing a compound of Formula 1 in water or ethanol and mixing with a volatile propellant and placing in a pressurized container having a metering valve to release a predetermined amount of material.

The liquefied propellant employed is one which has a boiling point below 65° F. at atmospheric pressure. For use in compositions intended to produce aerosols for medicinal use, the liquefied propellant should be non-toxic. Among the suitable liquefied propellants which may be employed are the lower alkanes containing up to five carbon atoms, such as butane and pentane, or a lower alkyl chloride, such as methyl, ethyl, or propyl, chlorides. Further suitable liquefied propellants are the fluorinated and fluorochlorinated lower alkanes such as are sold under the trademarks "Freon" and "Genetron". Mixtures of the above-mentioned propellants may suitably be employed. Examples of these propellants are dichlorodifluoromethane ("Freon 12"), dichlorotetrafluoroethane ("Freon 114"), trichloromonofluoromethane ("Freon 11"), dichloromonofluoromethane ("Freon 21"), dichloromonofluoromethane ("Freon 21"), monochlorodifluoromethane ("Freon 22"), trichlorotrifluoroethane ("Freon 113"), difluoroethane ("Genetron 142-A") and monochlorotrifluoromethane ("Freion 13").

The term "unit dosage form", as used in the specification and claims, refers to physically discrete units suitable as unitary dosages for human subjects and animals, each unit containing a predetermined quantity of active material calculated to produce the desired therapeutic effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are tablets, capsules, pills, coated tablet, powder packets, wafers, granules, cachets, teaspoonfuls, tablespoonfuls, dropperfuls, ampoules, vials, aerosols with metered discharges, segregated multiples of any of the foregoing, and other forms as herein described.

An effective but non-toxic quantity of the compound is employed in treatment. The dosage of the compound for treatment depends on the route of administration and the potency of the particular compound. A dosage schedule for humans of from about 0.05 to about 10 mg. of compound in a single dose, administered parenterally or by inhalation in the compositions of this invention, are effective for preventing allergy attacks. More specifically, the single dose is from about 0.5 to about 5 mg. of compound. The oral dose is from about 0.5 to about 30 mg. in a single dose. More specifically, the single dose is from about 1 to about 20 mg. of compound. The dosage to be administered can be repeated up to four times daily.

When repeated administration is desired, the compounds of this application which have a relatively short duration of activity can be administered in a priming dose-maintenance dose regimen as described in U.S. Ser. No. 382,762 now Pat. No. 3,993,679, at Page 58, line 19 to page 59, line 9.

The administration of the compositions of the present invention to humans and animals provides a method for the prophylactic treatment of allergy or all anaphylactic reactions, of a reagin or non-reagin mediated nature. That is to say, these compositions, when administered to a sensitized individual prior to the time that the individual comes into contact with substances (antigens) to which he is allergic, will prevent the allergic reaction which would otherwise occur. It is preferred to treat allergy of a reagin mediated nature.

Allergic conditions for which the process can be prophylactically employed are bronchial asthma, allergic rhinitis, food allergy, urticaria, exercise or stress induced asthma and anaphylactoid reactions. Preferred conditions are bronchial asthma, allergic rhinitis, food allergy and urticaria. More preferred conditions are bronchial asthma, allergic rhinitis and food allergy. Bronchial asthma and allergic rhinitis are the most preferred conditions.

EXAMPLE 10

One thousand tablets, each containing 10 mg. of ethyl 2'-hydroxy-3'-carboxy-5'-nitro oxanilate are prepared from the following types and amounts of ingredients:

| | |
|---|---|
| ethyl 2'-hydroxy-3'-carboxy-5'-nitro-oxanilate | 10 Gm. |
| Microcrystalline cellulose NF | 410 Gm. |
| Starch | 100 Gm. |
| Magnesium stearate power | 3 Gm. |

The ingredients are screened and blended together and pressed into tablets.

The tablets are useful to protect against food allergy at a dose of one tablet every four to six hours.

EXAMPLE 11

One thousand capsules, each containing 20 mg. of ethyl 2'-hydroxy-3'-carboxy-5'-nitro oxanilate are prepared from the following types and amounts of ingredients:

| | |
|---|---|
| ethyl 2'-hydroxy-3'-carboxy-5'-nitro oxanilate | 20 Gm. |
| Microcrystalline cellulose NF | 410 Gm. |
| Starch | 100 Gm. |
| Magnesium stearate powder | 3 Gm. |

The ingredients are screened and blended together and added to capsules.

The capsules are useful to protect against bronchial asthma at a dose of one capsule every four to six hours.

EXAMPLE 12

One thousand tablets, each containing 10 mg. of n-butyl 2'-hydroxy-3'-carboxy-5'-nitro oxanilate are prepared from the following types and amounts of ingredients:

| n-butyl 2'-hydroxy-3'-carboxy-5'-nitro oxanilate | 10 Gm. |
|---|---|
| Microcrystalline cellulose NF | 410 Gm. |
| Starch | 100 Gm. |
| Magnesium stearate powder | 3 Gm. |

The ingredients are screened and blended together and pressed into tablets.

The tablets are useful to protect against urticaria at a dose of one tablet every four to six hours.

EXAMPLE 13

One thousand tablets, each containing 20 mg. of isopropyl 2'-hydroxy-3'-carboxy-5'-nitro oxanilate are prepared from the following types and amounts of ingredients:

| isopropyl 2'-hydroxy-3'-carboxy-5'-nitro oxanilate | 20 Gm. |
|---|---|
| Microcrystalline cellulose NF | 410 Gm. |
| Starch | 100 Gm. |
| Magnesium stearate powder | 3 Gm. |

The ingredients are screened and blended together and pressed into tablets.

The tablets are useful to protect against food allergy at a dose of one tablet before meals.

EXAMPLE 14

A sterile preparation suitable for intramuscular injection and containing 0.5 mg. ethyl 2'-hydroxy-3'-carboethoxy-5'-nitro oxaniliate in each milliliter is prepared from the following ingredients:

| ethyl 2'-hydroxy-3'-carboethoxy-5'-nitro oxanilate | 0.5 | Gm. |
|---|---|---|
| Benzyl benzoate | 200 | ml. |
| Methylparaben | 1.5 | Gm. |
| Propylparaben | 0.5 | Gm. |
| Cottonseed oil q.s. | 1000 | ml. |

One milliliter of this sterile preparation is injected for prophylactic treatment of allergic rhinitis.

EXAMPLE 15

Six hundred ml. of an aqueous solution containing 2.0 mg. of the tris(hydroxymethyl)aminomethane salt of 2'-hydroxy-3'-carboxy-5'-nitro oxanilic acid, per ml. is prepared as follows:

| Tris (hydroxymethyl)aminomethane salt of 2'-hydroxy-3'-carboxy-5'-nitro oxanilic acid | 1.2 | Gm. |
|---|---|---|
| Sodium chloride | 5 | Gm. |
| Water for injection q.s. | 600 | ml. |

The compound of the above formulation and sodium chloride are dispersed in sufficient water to make 600 ml. and sterilized.

The liquid is placed in nebulizers designed to deliver 0.25 ml. per spray.

0.25 ml. of the liquid is inhaled into the lungs every four to six hours for prevention of asthmatic attacks.

EXAMPLE 16

A powder mixture consisting of 0.2 gram of the tris(-hydroxymethyl)aminomethane salt of 2'-hydroxy-3'-carboxy-5'-nitro oxanilic acid, and sufficient lactose to make five grams of mixture is micropulverized and placed in an insufflator designed to deliver 50 mg. of powder per dose.

A single dose of the powder is inhaled into the lungs every four to six hours for prevention of asthmatic attacks.

A single dose of the powder is inhaled intranasally every four hours for prevention of rhinitis.

EXAMPLE 17

A powder mixture consisting of 0.2 gram of the disodio salt of 2'-hydroxy-3'-carboxy-5'-nitro oxanilic acid, and sufficient lactose to make five grams of mixture is micropulverized and placed in an insufflator designed to deliver 50 mg. of powder per dose.

A single dose of the powder is inhaled into the lungs every four to six hours for prevention of asthmatic attacks.

A single dose of the powder is inhaled intranasally every four hours for prevention or rhinitis.

EXAMPLE 18

Twelve grams of an aerosol composition are prepared from the following ingredients:

| Tris(hydroxymethyl)-aminomethane salt of 2'-hydroxy-3'-carboxy-5'-nitro oxanilic acid | 0.750 Gm. |
|---|---|
| Freon 114 | 2.410 Gm. |
| Water | 6.300 Gm. |
| Sorbitan monoleate | 0.600 Gm. |

The compound is dispersed in water and added to the Freons. The twelve grams of composition are added to a 13 ml. plastic coated bottle and capped with a metering valve. The metering valve releases 80 mg. of composition in an aerosol. 80 mg. of the aerosol is inhaled every four to six hours for prevention of asthmatic attacks.

EXAMPLE 19

After allowing for the differing solubilities of the compounds and the activity of the particular compound as measured, for example, by the in vivo rat passive cutaneous anaphylaxis assay, a suitable quantity of each of the compounds of Examples 1–9 is substituted for the active compound in the compositions and uses of Examples 10–17. Results showing anti-allergy activity are obtained.

EXAMPLE 20

The rat passive cutaneous anaphylaxis assay is run in the following manner:

Female Sprague-Dawley 250 gm. rats are skin-sensitized with rat ani-ovalbumin homocytotropic anti-body that is heat labile and has a passive cutaneous anaphylaxis titer of 1:128. After a 72-hour latency period, the animals are challenged i.v. with 4 mg. ovalbumin (OA) + 5 mg. Evans blue dye and the test compound. If tested orally, the compound is suspended or dissolved in 0.25 percent methyl-cellulose in water and administered at the appropriate time interval before challenges. Thirty minutes later the extra-vascular bluing that results from antigen antibody combination at the skin site is read. Antibody dilutions are used such that in control animals a 4 mm spot is the lowest detectable spot, and 4 or 5 lower dilutions are used to give a range of antibody

We claim:
1. A compound of the formula

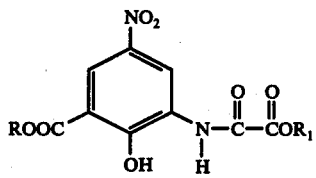

wherein R is hydrogen, a physiologically acceptable metal or amine cation or alkyl of one to eight carbon atoms, inclusive; $R_1$ is hydrogen, a physiologically acceptable metal or amine cation, or alkyl or one to eight carbon atoms, inclusive.

2. A compound in accordance with claim 1 wherein $R_1$ is alkyl of one to eight carbon atoms, inclusive.

3. A compound in accordance with claim 2 wherein R is the same as $R_1$.

4. A compound in accordance with claim 2 wherein R is hydrogen.

5. A compound in accordance with claim 4 wherein $R_1$ is from two to four carbon atoms, inclusive.

6. The compound in accordance with claim 5 wherein $R_1$ is ethyl.

7. A pharmaceutical composition which comprises an anti-allergy effective amount of a compound of the formula

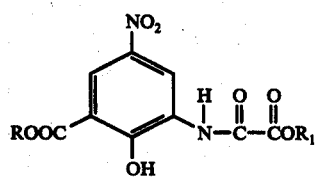

wherein R is hydrogen, a physiologically acceptable metal or amine cation or alkyl of one to eight carbon atoms, inclusive; $R_1$ is hydrogen, a physiologically acceptable metal or amine cation, or alkyl of one to eight carbon atoms, inclusive, in association with a pharmaceutical carrier.

8. A composition in accordance with claim 7 wherein the pharmaceutical carrier is suitable for oral administration.

9. A composition in accordance with claim 8 wherein the carrier is solid.

10. A composition in accordance with claim 8 wherein the carrier is liquid.

11. A composition in accordance with claim 10 wherein he carrier is aqueous.

12. A composition in accordance with claim 10 wherein the carrier is non-aqueous.

13. A composition in accordance with claim 8 wherein $R_1$ is alkyl of one to eight carbon atoms, inclusive.

14. A composition in accordance with claim 13 wherein R is hydrogen.

15. A composition in accordance with claim 14 wherein the carrier is solid.

16. A composition in accordance with claim 14 wherein the carrier is liquid.

17. A composition in accordance with claim 16 wherein the liquid is aqueous.

18. A composition in accordance with claim 16 wherein the liquid is non-aqueous.

19. A composition in accordance with claim 14 wherein $R_1$ is ethyl.

20. A method for treating mammals for allergy of a reagin medicated nature which comprises prophylactically administering to said mammal an anti-allergy effective amount of a compound of the formula

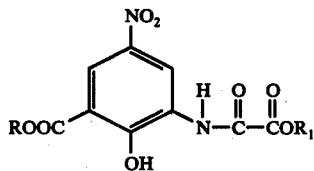

wherein R is hydrogen, a physiologically acceptable metal or amine cation or alkyl of one to eight carbon atoms, inclusive; $R_1$ is hydrogen, a physiologically acceptable metal or amine cation, or alkyl of one to eight carbon atoms, inclusive, in association with a pharmaceutical carrier.

21. A method in accordance with claim 20 wherein the administration is oral.

22. A method in accordance with claim 21 wherein the carrier is solid.

23. A method in accordance with claim 21 wherein the carrier is liquid.

24. A method in accordance with claim 23 wherein the carrier is aqueous.

25. A method in accordance with claim 23 wherein the carrier is non-aqueous.

26. A method in accordance with claim 21 wherein $R_1$ is alkyl of one to eight carbon atoms, inclusive.

27. A method in accordance with claim 26 wherein R is hydrogen.

28. A method in accordance with claim 27 wherein the carrier is solid.

29. A method in accordance with claim 27 wherein the carrier is liquid.

30. A method in accordance with claim 29 wherein the liquid is aqueous.

31. A method in accordance with claim 29 wherein the liquid is non-aqueous.

32. A method in accordance with claim 27 wherein $R_1$ is ethyl.

33. A composition in dosage unit form in accordance with claim 7.

34. A composition in accordance with claim 8 wherein $R_1$ is hydrogen.

35. A composition in accordance with claim 9 wherein $R_1$ is hydrogen.

36. A method in accordance with claim 20 wherein $R_1$ is hydrogen.

37. A method in accordance with claim 21 wherein $R_1$ is hydrogen.

38. A composition in accordance with claim 14 wherein the composition is a unit dose and is a tablet or a capsule.

39. A composition in accordance with claim 15 wherein the composition is a unit dose and is a tablet or a capsule.

40. A composition in accordance with claim 19 wherein the composition is a unit dose and is a tablet or capsule.

41. A method in accordance with claim 28 wherein a tablet or capsule is orally administered.

* * * * *